(12) United States Patent
Koehler et al.

(10) Patent No.: US 10,878,951 B2
(45) Date of Patent: Dec. 29, 2020

(54) SYSTEMS AND METHODS FOR PERFORMING AN ANALYSIS OF MEASURED BLOOD GLUCOSE VALUES

(75) Inventors: Matthias Koehler, Eckernfoerde (DE); Peter Blasberg, Weinheim (DE); Mariusz Tracz, Warsaw (PL)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 13/606,088

(22) Filed: Sep. 7, 2012

(65) Prior Publication Data

US 2013/0246096 A1    Sep. 19, 2013

(30) Foreign Application Priority Data

Sep. 9, 2011   (EP) .................................... 11180810

(51) Int. Cl.
  *G16H 10/00*   (2018.01)
  *G16H 80/00*   (2018.01)
  *G16H 15/00*   (2018.01)
  *G06F 19/00*   (2018.01)

(52) U.S. Cl.
  CPC ......... *G16H 15/00* (2018.01); *G06F 19/3456* (2013.01)

(58) Field of Classification Search
  CPC ........ G16H 50/70; G16H 10/60; G16H 50/20; G16H 50/50; G16H 10/20; G16H 15/00; G16H 40/67; G16H 50/80
  USPC .......................................................... 705/2, 3
  See application file for complete search history.

(56) References Cited

U.S. PATENT DOCUMENTS

| | | | |
|---|---|---|---|
| 5,912,656 A | 6/1999 | Tham et al. | |
| 6,949,073 B2 | 9/2005 | Sarel | |
| 2008/0007158 A1 | 3/2008 | Marcus et al. | |
| 2009/0006129 A1* | 1/2009 | Thukral | G16H 50/20 705/2 |
| 2010/0174553 A1* | 7/2010 | Kaufman et al. | 705/2 |
| 2011/0178820 A1* | 7/2011 | Soni et al. | 705/3 |

FOREIGN PATENT DOCUMENTS

| | | |
|---|---|---|
| DE | 102004057503 A1 | 6/2006 |
| WO | 2007112034 A3 | 10/2007 |
| WO | 2010072387 A2 | 7/2010 |
| WO | 2010149388 A3 | 12/2010 |
| WO | 2011060907 A1 | 5/2011 |

* cited by examiner

*Primary Examiner* — Trang T Nguyen
(74) *Attorney, Agent, or Firm* — Dinsmore & Shohl LLP

(57) ABSTRACT

A system and method for analyzing measured blood glucose values is disclosed, wherein the system includes a display device, a memory device, and a processor having program instructions which when executed cause the processor to provide blood glucose measurement information including a plurality of measured blood glucose values collected within a measurement time frame, perform a pre-analysis of the blood glucose measurement information, provide analysis data representing statistical blood glucose level information for the plurality of measured blood glucose values by performing an analysis of the plurality of measured blood glucose values, and provide output analysis data representing the analysis data, wherein the provision of analysis data and/or the provision of output analysis data are performed if, in the step of performing the pre-analysis, at least one of the following control checks is positive a fidelity check, and an adherence check.

20 Claims, 7 Drawing Sheets

SYSTEMS AND METHODS FOR PERFORMING AN ANALYSIS OF MEASURED BLOOD GLUCOSE VALUES

CROSS REFERENCE TO RELATED APPLICATIONS

The present U.S. utility patent application is related to and claims the priority benefit to European Patent Application Serial No. 11180810.1, filed Sep. 9, 2011, the contents of which are hereby incorporated by reference in their entirety into this disclosure.

BACKGROUND

The present disclosure relates generally to technologies in the field of diabetes care, especially an analysis system for performing an analysis of measured blood glucose values and a method for using the analyzing system.

Supporting patients by managing the characteristics of their measured blood glucose values often requires analytic techniques, such as a structured analysis. The objective of this analysis is to give the patient as well as the attending medical staff information which enables the patient to deal with his blood glucose values in an improved and appropriate manner. For people suffering from diabetes, in particular Diabetes Mellitus, it is especially important to keep their blood glucose values constantly at a particular level. A precondition for determining this information is knowing their blood glucose value, which may be measured using a blood glucose measuring device set up for this purpose. A blood glucose measuring device with which the blood glucose values of diabetics can be measured is known, for example from the document DE 10 2004 057 503 A1.

If it is determined, on the basis of the measured values, that the blood glucose value has exceeded a recommended level, medicine can be administered, for example by means of insulin injection or the oral administration of Metformin, an oral anti-diabeticum. If the blood glucose values fall below the ideal or recommended level, sugar can be orally ingested, for example through food or drink, to increase the blood glucose value. If the ideal level is exceeded for an extended period of time, there is the danger of serious health complications such as blindness, kidney damage, limbs having to be amputated or neuropathy. If the exceeding of the prescribed blood glucose level is considerable for a short time, this can lead to nausea, dizziness, sweating or even conditions of confusion. Thus, it is particularly important for a diabetic to have information about his blood glucose values so that he or the medical staff is able to implement appropriate measures to avoid the blood sugar values deviating from the ideal levels.

SUMMARY

The present disclosure comprises systems and methods for performing an analysis of measured blood glucose values.

An embodiment of a system for analysis of measured blood glucose values is provided, the system comprising a display device, a memory device, and a processor comprising program instructions which when executed cause the processor to:
provide blood glucose measurement information comprising a plurality of measured blood glucose values collected within a measurement time frame,
perform a pre-analysis of the blood glucose measurement information,
provide analysis data representing statistical blood glucose level information for the plurality of measured blood glucose values by performing an analysis of the plurality of measured blood glucose values, and
provide output analysis data representing the analysis data,
wherein the provision of analysis data and/or of provision of output analysis data are performed if, in the step of performing the pre-analysis, at least one of the following control checks is positive: a fidelity check, the fidelity check providing a positive result when the plurality of measured blood glucose values comprises a set of measured blood glucose values being representative for the measurement time frame, and an adherence check, the adherence check providing a positive result when the plurality of measured blood glucose values was collected in accordance with a testing scheme.

An embodiment of a method for performing an analysis of measured blood glucose values is also provided, the method comprising the steps of:
providing blood glucose measurement information comprising a plurality of measured blood glucose values collected within a measurement time frame,
performing a pre-analysis of the blood glucose measurement information,
providing analysis data representing statistical blood glucose level information for the plurality of measured blood glucose values by performing an analysis of the plurality of measured blood glucose values, and
providing output analysis data representing the analysis data, wherein the step of providing analysis data and/or the step of providing output analysis data are performed if, in the step of performing the pre-analysis, at least one of the following control checks has been positively performed:
a fidelity check, the fidelity check providing a positive result when the plurality of measured blood glucose values comprises a set of measured blood glucose values being representative for the measurement time frame, and
an adherence check, the adherence check providing a positive result when the plurality of measured blood glucose values was collected in accordance with a testing scheme.

According to at least one embodiment of the present disclosure, the analysis is a structured analysis.

In at least one embodiment of the present disclosure, in the course of the analysis, at least one blood glucose statistical parameter selected from the following group of parameters is provided: a mean blood glucose value, a low/high blood glucose index, and a standard deviation.

In an embodiment of the present disclosure, from the plurality of measured blood glucose values, a set of measured blood glucose values being representative for the measurement time frame is selected, and the analysis for the selected set of measured blood glucose values is performed.

In at least one embodiment of the present disclosure, a positive result of the fidelity check is provided if a threshold value is fulfilled by the plurality of measured blood glucose values. In at least one exemplary embodiment, a threshold value, for example a number of measured blood glucose values per time period or a minimum number of tests, is defined according to which the plurality of measured blood glucose values is considered as being representative and trustful, or as being insufficient. The threshold could be different for the different test schemes or measurement time frames. If the set of measured blood glucose values is found insufficient (not representative), the parameters provided by the analysis could either not be displayed at all, or only some of them, or in an altered way and/or with a disclaimer to indicate that it might not be representative for the whole time frame period.

In at least one embodiment of the present disclosure, a positive result of the fidelity check is provided if, for the plurality of measured blood glucose values, at least one of following testing parameters is fulfilled: overall frequency of testing events over the measurement time frame, frequency of testing events per day, frequency of testing events per week, frequency of testing events per month, and maximum/minimum time interval between successive testing events. The fidelity check may comprise checking a test frequency (TF), test frequency of testing days and/or testing behavior. For example, the testing behavior describes a distribution of blood glucose testing events over the time of the day. For example, the 24 hours of the day can be divided in several time blocks (also referred to as "measured time frame(s)"), e.g., before breakfast, after breakfast, and before and after lunch. The test frequency for each time block is calculated, or the time stamp assigned to each measured blood glucose value is used, and the distribution of the testing events over the day is calculated.

According to at least one embodiment, the testing scheme is provided by at least one of
- deriving information about the testing scheme from an analysis of the pre-analysis of the blood glucose measurement information,
- deriving information about the testing scheme from structured analysis of the plurality of measured blood glucose values,
- deriving information about the testing scheme from a therapy type, and
- deriving information about the testing scheme from a user input received via an input terminal connected to the processor.

In the step of deriving, as defined herein, the respective information is inferred or gathered by analyzing, processing and/or looking up electronic data.

In at least one embodiment, the analyzing system is implemented in a blood glucose measurement system, or a data analysis system.

With respect to embodiments of the method for performing the analysis of measured blood glucose values in the analyzing device, the aspects described above in relation to embodiments of the system for analysis (or analyzing device, as may be used) apply accordingly.

DRAWINGS

The features and advantages of the present disclosure, and the manner of attaining them, will be more apparent and better understood by reference to the following descriptions taken in conjunction with the accompanying figures, wherein.

DETAILED DESCRIPTION

Figure 1:
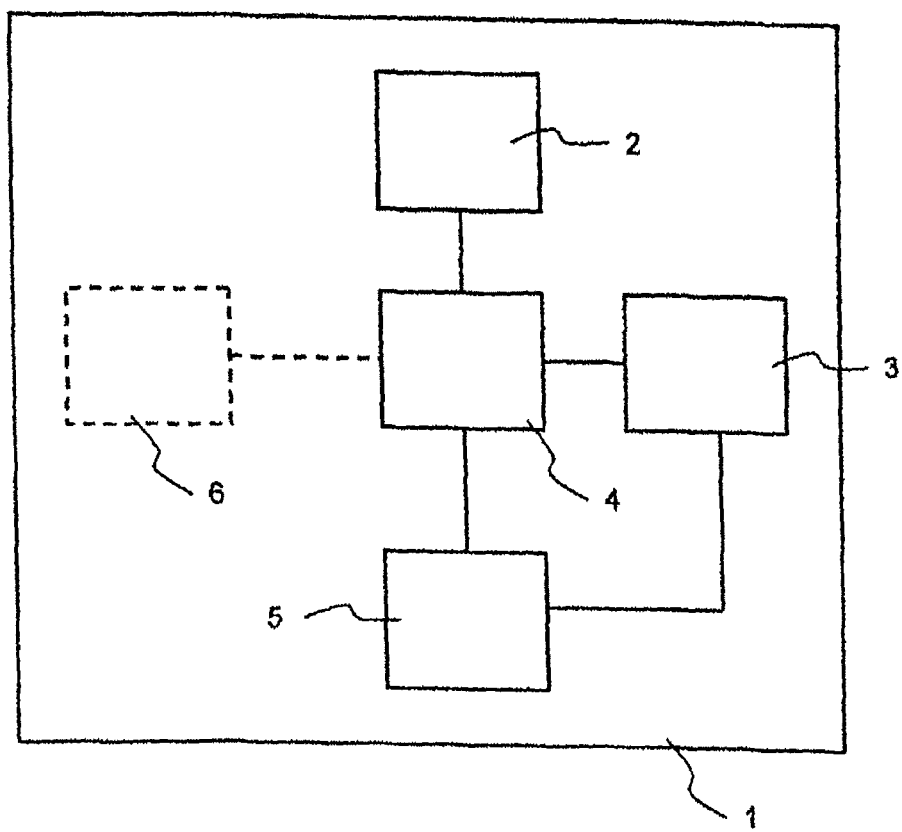
FIG. 1 shows a schematic representation of an analyzing device, according to at least one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Generally, the present disclosure provides systems and methods for performing an analysis of measured blood glucose values. FIG. 1 shows a schematic representation of an analyzing device 1 (also referred to herein in various embodiments as an "analyzing system" or "a system for analyzing measured blood glucose values") configured for performing an analysis of a plurality of measured blood glucose values. This analysis according to at least one embodiment may be a structured analysis. The analyzing device 1 is provided with a display 2, a memory 3, and a processor 4 connected to the display 2 and the memory 3. An application module 5 is implemented, the application module 5 comprising program instructions which when executed by the processor 4 causes the processor 4 to perform an analysis of the plurality of measures blood glucose values provided in the analyzing device 1. The analyzing device may comprise one or more functional modules or elements 6, for example an interface for wireless data transmission.

The analyzing device 1 may be provided in any kind of data system configured for electronic data processing. For example, the analyzing device 1 may be implemented in a blood glucose measurement system configured to collect measurement data for the blood glucose level of a patient or user. In another embodiment, the analyzing device 1 may be implemented in a personal computer or a mobile device, like e.g. a smart phone. In this and other embodiments the plurality of measured blood glucose values may be transferred from the measurement system to the personal computer by wireless or wired data transfer. Also, a data storage element such as a CD, a SD card or a USB stick may be used for data transfer.

Figure 2:
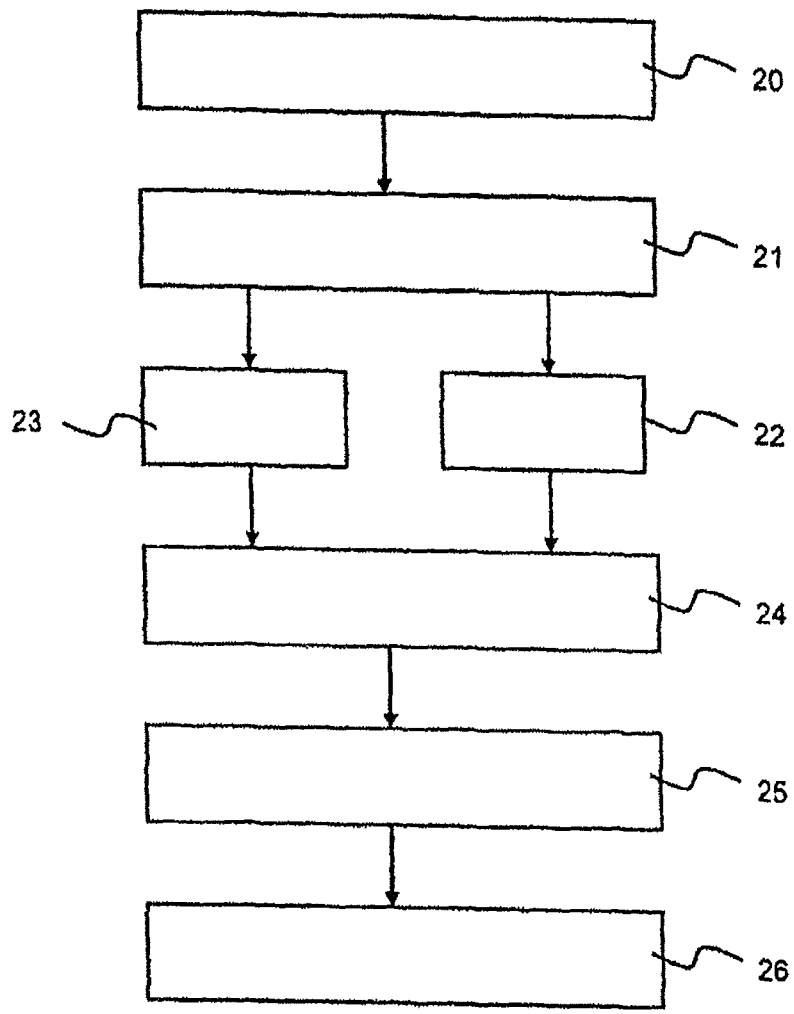
FIG. 2 shows a schematic representation of a process of operating the analyzing device, according to at least one embodiment of the present disclosure.

FIG. 2 shows a schematic representation for an operation process of the analyzing device 1 based on program instructions provided in the application module 5. The program instructions, when executed by the processor 4, cause the processor 4 to perform the following steps. In step 20, blood glucose measurement information comprising a plurality of measured blood glucose values collected within a measurement time frame is provided. The measured blood glucose values each represent a measured blood glucose value taken at a testing event. In step 21, a pre-analysis of the blood glucose measurement information is started. In the course of the pre-analysis, a fidelity check is performed in step 22. The fidelity check assesses whether the plurality of measured blood glucose values provided before comprises or in total provides a set of measured blood glucose values being "representative" for the measurement time frame. The fidelity check is successful if such representative set of measured blood glucose values is identified in the pre-analysis. For example, a set of measured blood glucose values may be considered as being representative if a defined number (threshold) of values is provided. Such threshold may define a necessary number of values per time block. In addition, or as an alternative, a criterion for sufficient statistical confidence may be applied for deciding about whether the set of values is representative. In this respect, the confidence coefficient or the confidence level may be considered. The meaning of the term "confidence level" is that, if confidence intervals are constructed across many separate data analyses of repeated (and possibly different) experiments, the proportion of such intervals that contain the true value of the parameter will approximately match the confidence level; this is guaranteed by the reasoning underlying the construction of confidence intervals.

As an alternative, or in addition to the fidelity check of step 22, an adherence check may be initiated by the program instructions running on the processor 4 in step 23. In at least one embodiment of the present disclosure, the adherence check tests whether the plurality of measured blood glucose values was collected in accordance with a testing scheme. The adherence check is successful if the plurality of measured blood glucose values provides a set of measured blood glucose values which were collected according to a selected testing scheme. The testing scheme itself may be identified in the pre-analysis from an analysis of the blood glucose measurement information. For example, from the information indicating a time scheme for collecting the plurality of measured blood glucose values a respective testing scheme may be identified. Also, a testing scheme to be checked against the blood glucose measurement information may be selected in response to a user input to the analyzing device 1.

If at least one of the fidelity check and the adherence check provides a successful result, analysis data representing statistical blood glucose level information for the plurality of measured blood glucose values is provided by performing a structured analysis of the plurality of measured blood glucose values (step 24).

In step 25, output analysis data representing the analysis data derived before are provided for outputting to the user, for example via the display 2 of the analyzing device 1. Also, the output analysis data may be transferred for outputting from the analyzing device 1 to another output device. Also, electronic information assigned to the analysis data may be stored in the memory 3. The output analysis data are outputted in step 26.

The analysis data provided by the analysis, which in an exemplary embodiment is a structured analysis, may comprise different statistical parameters derived from the plurality of measured blood glucose values. In at least one exemplary embodiment, such diabetes related statistical analysis values do not refer to single discrete measured blood glucose values, but characterize the whole set of measured blood glucose data collected in the measurement time frame. In general, the term "statistical parameters" as used here can be any parameter representing, different from a single measured value, a calculated value derived from at least two measured blood glucose values.

The analysis data may characterize a set of data describing and/or summarizing a medical and therapeutically relevant aspect of the measured blood glucose values, e.g. the mean blood glucose level (MBG), a low/high blood glucose index (LBGI/HBGI), and/or standard deviation (SD). For example, patients' blood glucose situation as derivable from the plurality of measured blood glucose values can be summarized using the mean blood glucose level to describe the general level of the measured data. In another example, the standard deviation may indicate glycemic variability, and the low blood glucose index may be used to describe a hypoglycemia (also referred to herein as "hypo") risk.

Also, other variability parameter could be used instead of the standard deviation, e.g. mean amplitude of glycemic excursions (MAGE), and/or average daily risk range (ADRR). To describe the hypo risk, the absolute numbers of hypoglycemia can be provided with the analysis data. HBGI describing the hyper glycemia risk can also be added as an additional parameter or instead of MBG.

The provision of analysis data representing statistical blood glucose level information instead of discrete single blood glucose values has the advantage that the user or the patient only needs to read and understand a few, e.g. three, numbers instead of e.g. several hundred data points representing the measured blood glucose values. For example, a favorable analysis parameter is the HbAlc describing the average blood glucose level over the last eight to twelve weeks. It has the advantage of being only one single number compared to the hundreds of measurement data collected.

In at least one embodiment of the present disclosure, the fidelity check and/or the adherence check may be used as the only requirement(s) for performing the step of providing analysis data and/or the step of providing output analysis data.

By the fidelity check it may be verified whether the plurality of measured blood glucose values is representative for the measurement time frame, i.e., the set of measured data which is to be used in the step of providing the analysis data by the analysis must be representative for the measurement time frame. This is especially important in view of the fact that (only) statistical blood glucose level information is provided to the user, and the user does not see the measured blood glucose value behind the outputted parameters. In contrast, when the discrete measured data itself are displayed, the user can see and decide themself if the outputted data are representative. For example, if the MBG over three months is calculated but only a few measured blood glucose values are available for that time period, the MBG parameter as such can still be calculated, but the data are most likely not representative for the whole time period under consideration and might lead to a medical misinterpretation. The statistical parameter itself, however, always remains unchanged, e.g. one value for the MBG, independently if it is calculated out of 5 or 500 data points.

To overcome this problem, in at least one exemplary embodiment the pre-analysis step the blood glucose measurement information is analyzed as to whether the plurality of measured blood glucose values available for the structured analysis to follow is representative for the measurement time frame. Such step of verification is referred to as fidelity check. Following steps, namely the step of providing analysis data and/or the step of providing output analysis data are performed only if, in the step of performing the pre-analysis, at least one of the fidelity and the adherence check has been successfully completed.

In the adherence check, the actual testing behavior derivable for the plurality of measured blood glucose values from the blood glucose measurement information may be compared to a recommended testing scheme. For example, a testing scheme may be to collect a blood glucose value each day before breakfast, before lunch, before dinner and at bedtime. The testing scheme usually correlates with a therapy type. Therapy types are e.g. using only oral anti-diabetic drug (OAD), 1 to 2 daily insulin injections or insulin pump therapy. General information as to the aspect of adherence in the field of customized disease self-management may be taken from the document WO 2010/149388 A2. Especially, terms like, for example, adherence, adherence measurement, adherence to prescribed therapy rules, and compliance to a procedure are explained in further detail in said document which is fully incorporated here by reference.

In at least one embodiment of the present disclosure, predefined therapy types and/or predefined testing schemes are provided by the analyzing device. They could be based on international or national guidelines and/or the user can define them. The analyzing device could automatically recognize and propose a therapy type or testing scheme based on the data distribution derivable from the blood glucose measurement information. Following, such automatically recognized information may be used in at least one of the fidelity check and the adherence check. In another embodiment, the user may be asked to set the therapy type for his patient. In both cases, the analyzing device could assess the adherence or compliance of the patient, i.e. it compares the testing scheme with the actual testing behavior. It could display the adherence, e.g. by calculating and highlighting the discrepancies, e.g. the times of the day where the patient should have been tested but didn't or did not enough. The testing scheme can be selected e.g. according to the type of diabetes.

In at least one embodiment, at least one of the fidelity check and the adherence or compliance check is not only used to define if or how the parameter(s) derived in the structured analysis is/are displayed, but also as a feedback to the user. Some check result information is generated by the processor and outputted to the user. This could be used as motivational and/or educational tool. The feedback can contain color codes like traffic light colors and/or icons or numbers, e.g. "☺ you are 90% adherent to your test scheme", "you measure regularly at breakfast, but you should measure more frequent after lunch". The check result information may exclusively inform about the check result(s) as such, but may also comprise some user guidance information depending on the check result to improve future testing, for example.

In at least one embodiment, if the pre-analysis provides that the plurality of measured blood glucose values is only representative for a time period shorter than the measurement time frame, an adjusted time frame, which preferably corresponds to the shorter time period identified before, is used for the fidelity check and/or the adherence check. Also, the adjusted time period may be used in the analysis, preferably being a structured analysis. For example, if there is a measurement time frame of eight weeks, but there are only measured blood glucose data for a period of four weeks, the analyzing device may adjust the period to that four weeks. Alternately, if there are only morning values available the system could limit the parameters to such time block.

The application module may comprise program instructions which when executed by the processor cause the processor to perform the fidelity check and the adherence check at least in part at the same time. However, these checks may also be performed one after the other.

Referring now to FIGS. 3 to 7, different schematic representations of a screen displaying output analysis data derived from the structured analysis of the plurality of measured blood glucose values are explained in the following. In FIGS. 3 to 7, for the same feature identical reference numerals are used.

Figure 3:
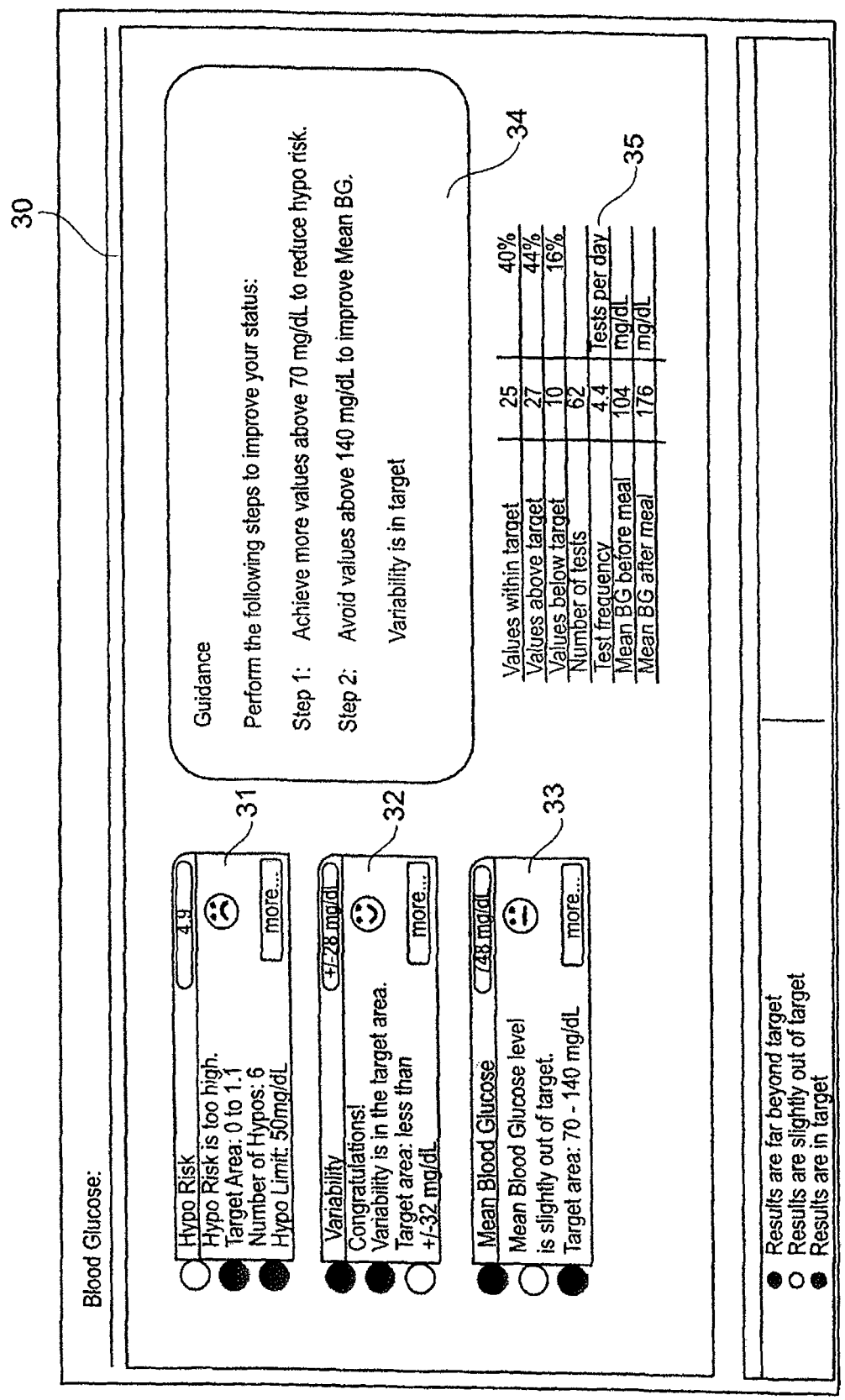
FIG. 3 shows a schematic representation of a screen displaying output analysis data comprising different statistical parameters, according to at least one embodiment of the present disclosure.

FIG. 3 shows a schematic representation of an embodiment of screen 30 displaying output analysis data comprising different statistical parameters. The following statistical parameters derived in the course of the structured analysis of the plurality of measured blood glucose values are displayed: a hypo risk parameter 31, a variability parameter 32, and a mean blood glucose parameter 33. The statistical parameters each are displayed together with a color code. The color code gives the user additional indication as to whether the respective statistical parameter derived in the structured analysis is within a given target limit or not. For example, a red color code may be provided for a statistical parameter which is not within the target value limits. A green color code may be used for indicating that the respective statistical parameter is within the target limits. A yellow code may indicate that a statistical parameter is still within or slightly outside the target limits.

In FIG. 3, in addition, some guidance information 34 for the user is displayed. The guidance information 34 is derived and selected in dependence on the displayed statistical parameters 31, 32, 33. Also, on the screen in FIG. 3 further analysis information is presented in a table 35. In the embodiment presented in FIG. 3, information about the number of measured blood glucose values which are within, above and below target limits is shown.

Figure 4:
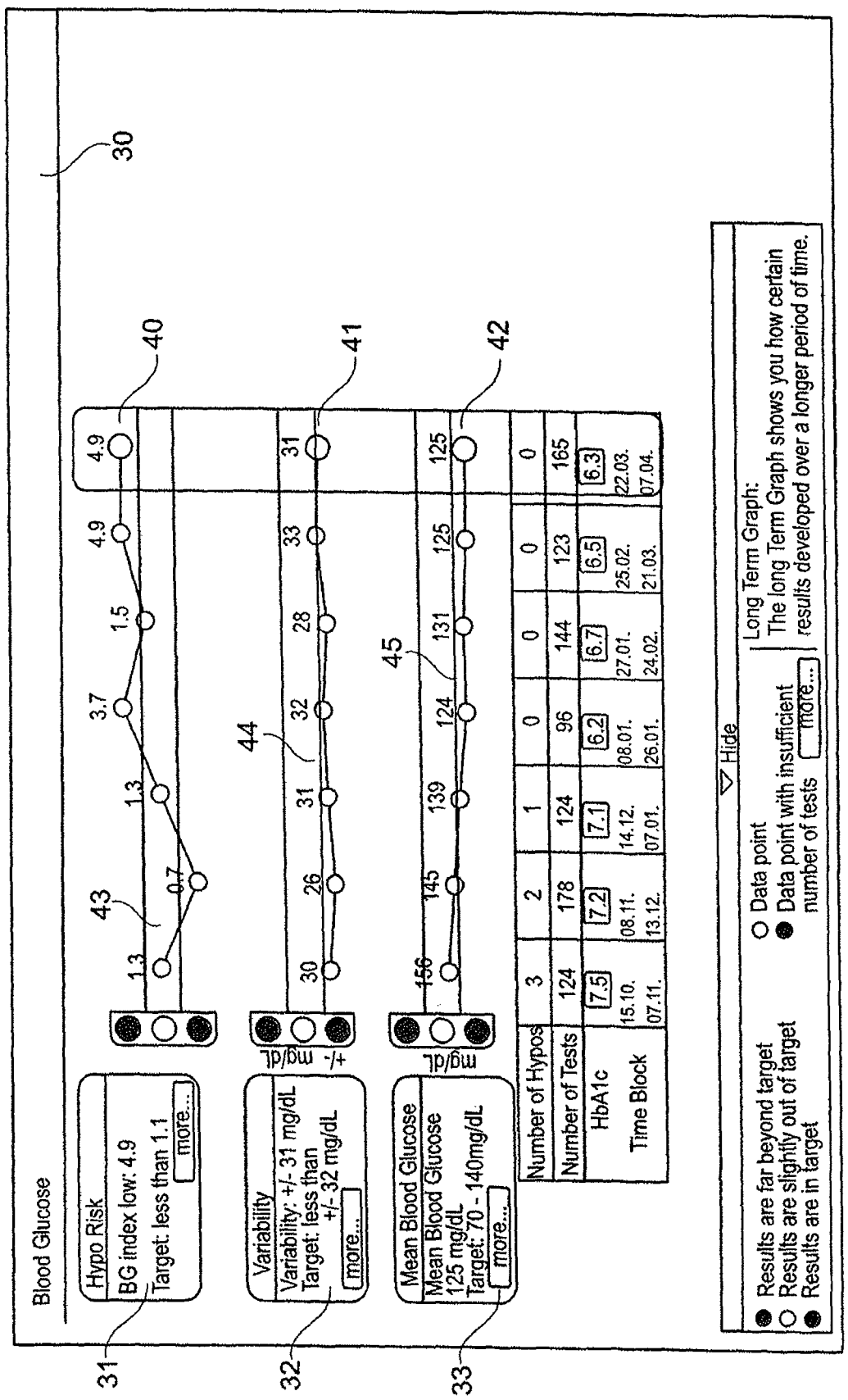
FIG. 4 shows a schematic representation of a screen displaying output analysis data comprising different statistical parameters for several time frames, according to at least one embodiment of the present disclosure.

FIG. 4 shows a schematic representation of an embodiment of screen 30 displaying output analysis data comprising different statistical parameters for several time frames. On the left hand side of the screen 30 in FIG. 4 the following statistical parameters derived from the structured analysis of the plurality of measured blood glucose values are presented: the hypo risk parameter 31, the variability parameter 32, and the mean blood glucose parameter 33. Each of the statistical parameter is assigned a graphical representation 40, 41, 42 which shows data for each of the statistical parameters 31, 32, 33 referring to older time periods. Present data 43, 44, 45 for each of the statistical parameters, again, may be displayed with a color code. Such optional color code as may be used in any or all of FIGS. 3-7 is described in further detail herein.

Figure 5:
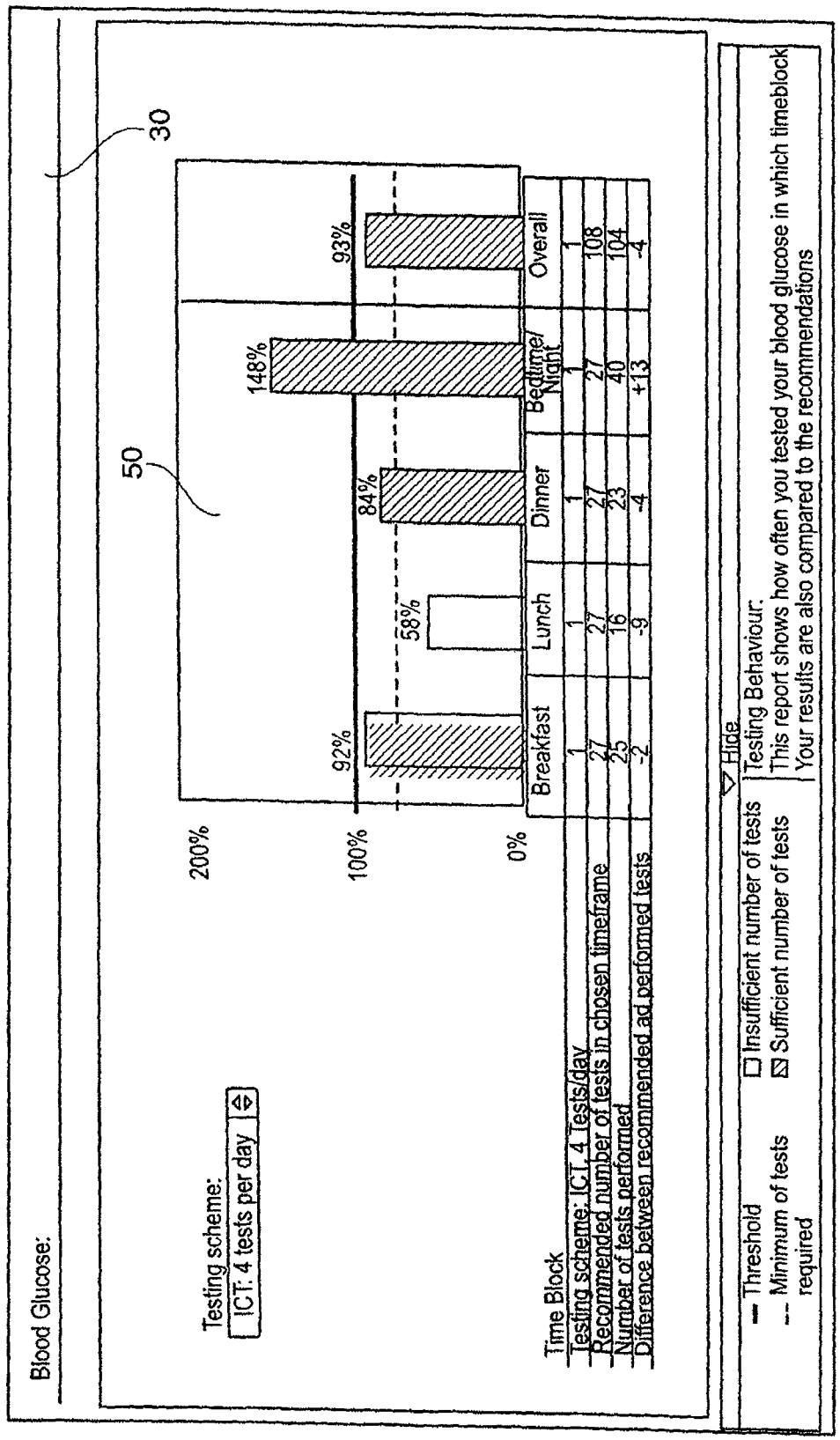
FIG. 5 shows a schematic representation of a screen displaying output analysis data relating to a selected testing scheme, according to at least one embodiment of the present disclosure.

FIG. 5 shows a schematic representation of an embodiment of screen 30 displaying output analysis data comprising different statistical parameters for several time frames. The result of a testing scheme analysis is presented. The following parameters are displayed: test frequency, time block, testing scheme, recommended number of tests in chosen timeframe, number of tests performed, and difference between recommended and performed tests. A column diagram 50 represents the result of the analysis as to the recommended (required) number of blood glucose testing events compared to the tests actually performed. The recommended number of tests (100%) was only achieved for the time block "Bedtime/Night". The threshold for the acceptable number of tests, here 80% of the recommended number of tests in the exemplary embodiment depicted, was achieved for the time blocks "Breakfast" and "Dinner". For the time block "Lunch" the number of blood glucose measurements does not even reach the minimum number of tests required.

Figure 6:
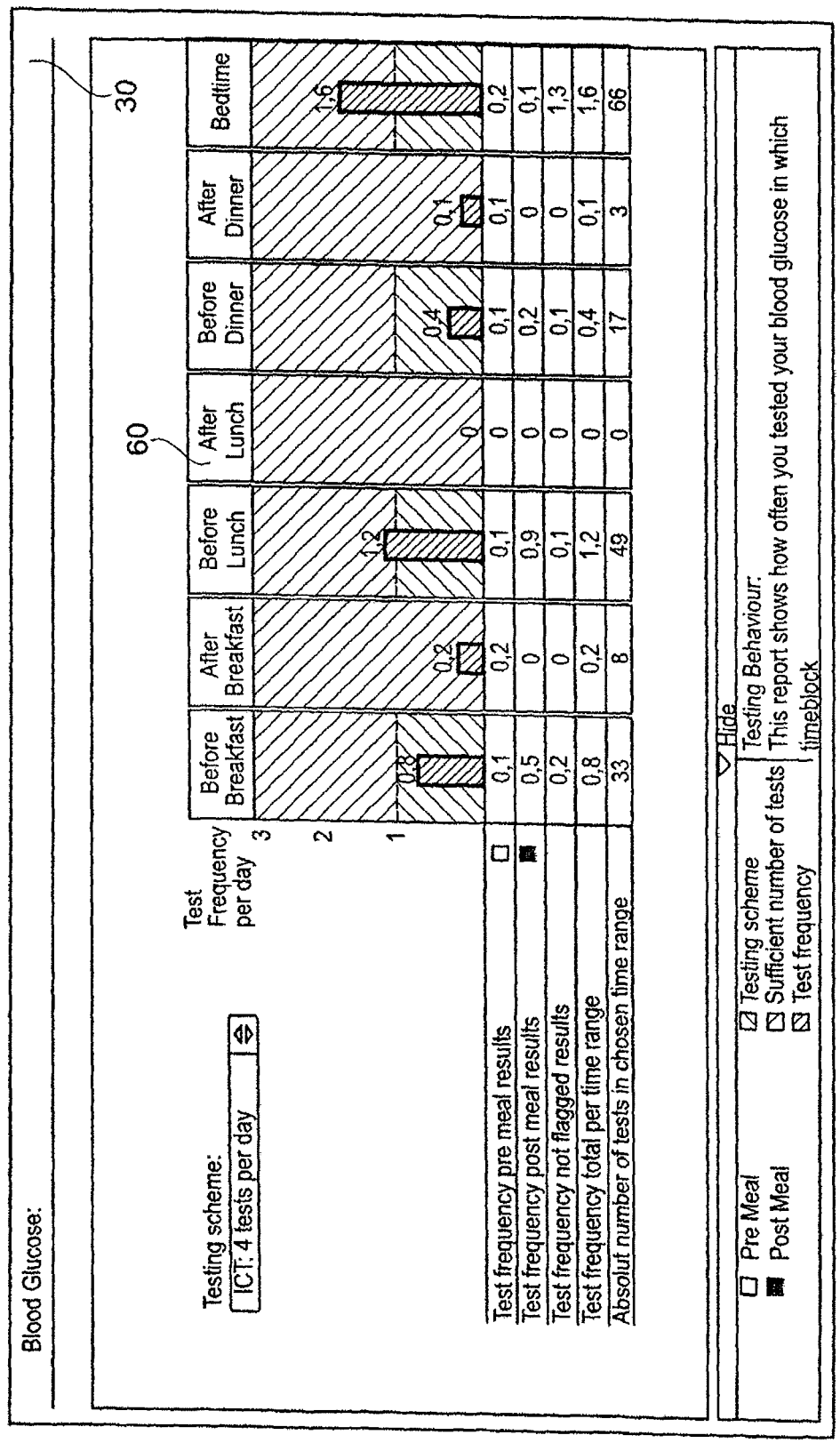
FIG. 6 shows a schematic representation of a screen displaying output analysis data relating to a selected testing scheme, according to at least one embodiment of the present disclosure.

FIG. 6 shows a schematic representation of an embodiment of screen 30 displaying output analysis data comprising different statistical parameters for several time frames. Again, the result for a testing scheme analysis is displayed. For different time blocks 60 the following data are identified: test frequency pre meal results, test frequency post meal results, test frequency not flagged results, test frequency total per time range, and absolute number of tests in chosen time range. For two time blocks, namely time block "Before Lunch" and time block "Bedtime", a test frequency of more than one was identified. For the time block "After Lunch" no measured blood glucose value could be identified.

Figure 7:
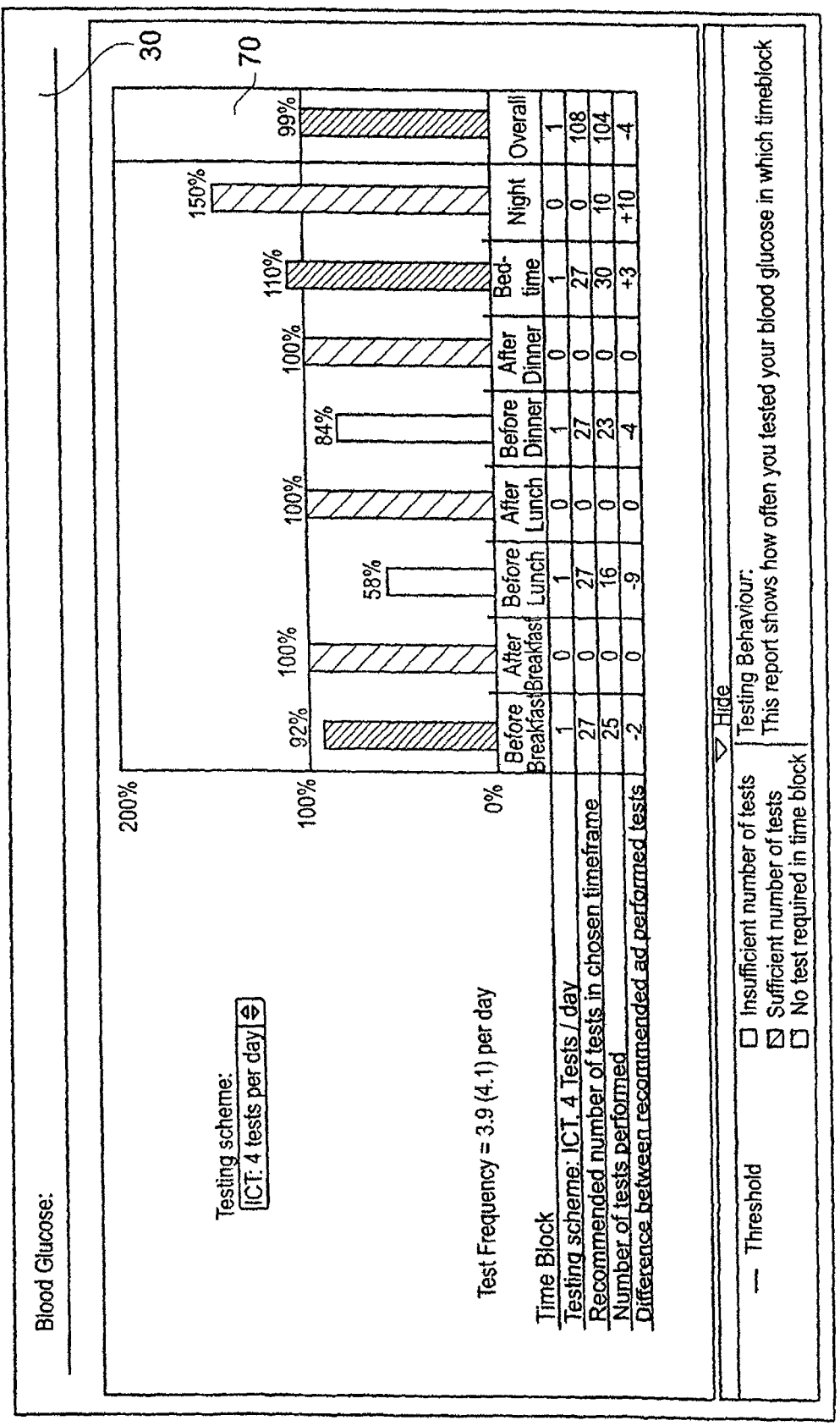
FIG. 7 shows a schematic representation of a screen displaying output analysis data relating to a selected testing scheme, according to at least one embodiment of the present disclosure.

FIG. 7 shows a schematic representation of an embodiment of screen 30 displaying output analysis data comprising different statistical parameters for several time frames. Another result for a testing scheme analysis which provides information for the adherence check is represented. The representation of the data identified, in part, is comparable to FIG. 5. However, additional time blocks are provided in FIG. 7. The information whether there is a sufficient number of testing events in a given time block is shown in the graphical representation 70. Also, a color code is used which is explained on the bottom of the screen in FIG. 7. For the time blocks "Before Breakfast", "Before Lunch", and "Before Dinner" there is no sufficient number of measured blood glucose values.

In at least one embodiment of the present disclosure, the output analysis data are provided with a color code. To make interpretation of the outputted analysis data for the user, namely a patient or medical staff, easier color codes can be used, e.g. green when the statistical value is in a target range, yellow when it is slightly out of target and red when it is significantly out of target range. As different statistical blood glucose parameters may indicate a certain separated aspect of the metabolic situation, the user can easily identify which aspect is fine and which aspect needs to be improved. The parameters might also be prioritized to guide the user which step should be done first. For example, if a first, a second and a third blood glucose parameter are outputted with red, yellow and green color code, respectively, the recommendation is to first improve the first blood glucose parameter, then the second blood glucose parameter. As the third blood glucose parameter is in target, no further optimization is needed.

In an exemplary embodiment, the first, the second and the third blood glucose parameter are outputted with yellow, red and red color code, respectively, and the there is, e.g. due some specific therapy scheme, a blood glucose parameter priority to fix the first blood glucose parameter first, then the second blood glucose parameter, then the third blood glucose parameter. In such case, the overall recommendation to the user is to firstly fix the second blood glucose parameter, then the third blood glucose parameter, then the first blood glucose parameter.

For further support for diabetes self-management, e.g. the therapy, a guidance text recommending the next step(s) can be provided together with the output analysis data. The guidance text can depend on the individual status of each parameter outputted and can, e.g. depending on an evaluation matrix, provide recommendations specific for each situation. The evaluation matrix may assign specific recommendation text to specific parameter result calculated in the structured analysis.

While various embodiments of systems for analyzing blood glucose values and methods for using the same have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A system for analyzing measured blood glucose values of a diabetic and providing statistical blood glucose level information based on the measured blood glucose values, the system comprising:
   a display,
   a memory device,
   an application module comprising program instructions, and
   a processor connected to the display, the memory and the application module, said program instructions which when executed cause the processor to:
      provide blood glucose measurement information which comprises plurality of measured blood glucose values collected within a measurement time frame,
      perform a pre-analysis of the blood glucose measurement information,
      provide analysis data representing statistical blood glucose level information for the plurality of measured blood glucose values via an analysis performed by the processor with the plurality of measured blood glucose values, the analysis performed in response to the pre-analysis comprising a positive result for each of a fidelity check and an adherence check on the plurality of measured blood glucose values, the positive result for the fidelity check indicative that a threshold number of measured blood glucose values is provided and meet a confidence level, in which the confidence level is met by a proportion of the threshold number of measured blood glucose values being contained in a confidence interval constructed from experimental data that matches the confidence level, and the positive result for the adherence check indicative that the plurality of measured blood glucose values are collected in accordance with a testing scheme, and
      provide as output of the system, output analysis data that represents the analysis data on the display, wherein the output analysis data comprises statistical blood glucose level information which characterizes a whole set of the measured blood glucose values collected in the measurement time frame instead of discrete single blood glucose values, wherein the processor performs the analysis and/or provides the output analysis data only upon, in performance the pre-analysis, the fidelity check being positive for the measurement time frame, in which the processor provides the positive result for the fidelity check upon the plurality of measured blood glucose values comprising a set of measured blood glucose values being representative for the measurement time frame such that the statistical blood glucose level information, represented by the analysis data and provided by the processor on the display as the output analysis data, is only based on the measured blood glucose values which have a positive fidelity check, and wherein upon the pre-analysis providing that the plurality of measured blood glucose values is only representative for a time period shorter than the measurement time frame, an adjusted time frame which corresponds to the shorter time period identified by the processor is then used by the processor as the measurement time frame for the fidelity check such that the statistical blood glucose level information based on the whole set of the measured blood glucose values and displayed on the display by the processor as the output analysis data is representative only for the time period shorter than the measurement time frame.

2. The system of claim 1, wherein the analysis is a structured analysis.

3. The system of claim 1, wherein in the course of the analysis, at least one blood glucose statistical parameter selected from the following group of parameters is provided on the display by the processor: a mean blood glucose value, a low/high blood glucose index, and a standard deviation.

4. The system of claim 1, wherein the set of measured blood glucose values being representative for the measurement time frame is selected by the processor from the plurality of measured blood glucose values, and wherein the analysis for the selected set of measured blood glucose values is performed by the processor.

5. The system of claim 1, wherein the positive result for the fidelity check is provided upon a threshold value being fulfilled by the plurality of measured blood glucose values.

6. The system of claim 1, wherein the positive result for the fidelity check is provided upon, for the plurality of measured blood glucose values, at least one of following testing parameters being fulfilled: overall frequency of testing events over the measurement time frame, frequency of testing events per day, frequency of testing events per week, frequency of testing events per month, and maximum/minimum time interval between successive testing events.

7. The system of claim 1, wherein the output analysis data are provided with a color code.

8. The system of claim 1, wherein the testing scheme is provided by at least one of:
information about the testing scheme derived from an analysis of the pre-analysis of the blood glucose measurement information,
information about the testing scheme derived from structured analysis of the plurality of measured blood glucose values,
information about the testing scheme derived from a therapy type, and
information about the testing scheme derived from a user input received via an input terminal connected to the processor.

9. The system of claim 1, implemented in a blood glucose measurement system configured to collect from the patient the plurality of measured blood glucose values, a personal computer, a mobile device, a smart phone, or a data analysis system.

10. The system of claim 1, wherein an adherence check is performed by the processor in performance of the pre-analysis, and in addition to the fidelity check being positive, upon the adherence check being positive for the measurement time frame the processor then performs the analysis and/or provides the output analysis data, wherein the processor provides a positive result for the adherence check upon the plurality of measured blood glucose values being collected in accordance with a testing scheme.

11. The system of claim 10, wherein at least one of the fidelity check and the adherence check is used by the processor to define whether or how a parameter derived in a structured analysis is displayed on the display, and/or to provide feedback on the display.

12. The system of claim 10, wherein upon the pre-analysis providing that the plurality of measured blood glucose values is only representative for a time period shorter than the measurement time frame, the adjusted time frame which corresponds to the shorter time period identified by the processor is also used for the adherence check.

13. The system of claim 1, wherein information assigned to the analysis data is stored in the memory device.

14. The system of claim 1, wherein a screen is provided by the processor on the display, wherein the screen displays the statistical blood glucose level information provided in the output analysis data as statistical parameters comprising a hypo risk parameter, a variability parameter, and a mean blood glucose parameter, and wherein each of the statistical parameters are displayed together with a color code to indicate as to whether each respective statistical parameter is within a given target limit, not within the target value limit, and slightly outside the target limit.

15. The system of claim 14, wherein a screen is provided by the processor on the display, wherein the screen displays guidance information derived and selected by the processor in dependence on the displayed statistical parameters, and further analysis information about number of measured blood glucose values which are within, above and below target limits and/or the adherence check.

16. The system of claim 14, wherein a screen is provided by the processor on the display, wherein the screen displays the statistical parameters for several time frames, wherein each of the statistical parameter is assigned a graphical representation which shows data for each of the statistical parameters referring to older time periods than the time period under consideration.

17. The system of claim 1, wherein a screen is provided by the processor on the display, wherein the screen displays the statistical blood glucose level information provided in the output analysis data as statistical parameters for several time frames each comprising test frequency, time block, testing scheme, recommended number of tests in chosen timeframe, number of tests performed, and difference between recommended and performed tests.

18. The system of claim 1, wherein a screen is provided by the processor on the display, wherein the screen displays the statistical blood glucose level information provided in the output analysis data as statistical parameters for several time frames each comprising a time block, wherein the time block is selected from a time block "Before Breakfast", a time block "After Breakfast", a time block "Before Lunch", a time block "After Lunch", time block "Before Dinner", a time block "After Dinner", and a time block "Bedtime", and for each time block the output analysis data identified therewith comprises test frequency pre-meal results, test frequency post meal results, test frequency not flagged results, test frequency total per time range, and absolute number of tests in chosen time range.

19. A method improving statistical blood glucose level information provided to a diabetic by a system performing an analysis of measured blood glucose values from the diabetic, the method comprising the steps of:
   providing as input blood glucose measurement information to a processor, the blood glucose measurement information comprising a plurality of measured blood glucose values collected within a measurement time frame,
   performing a pre-analysis of the blood glucose measurement information using the processor,
   providing analysis data representing statistical blood glucose level information which characterizes a whole set of the measured blood glucose values collected in the measurement time frame instead of discrete single blood glucose values by performing an analysis of the plurality of measured blood glucose values using the processor, the analysis performed in response to the pre-analysis comprising a positive result for a fidelity check on the plurality of measured blood glucose values, the positive result for the fidelity check indicative that a threshold number of measured blood glucose values is provided and meet a confidence level, in which the confidence level is met by a proportion of the threshold number of measured blood glucose values being contained in a confidence interval constructed from experimental data that matches the confidence level, and
   providing as output from the processor output analysis data representing the analysis data to a display,
   wherein the step of performing an analysis of the plurality of measured blood glucose values and/or the step of providing the output analysis data are performed by the processor only upon, in the step of performing the pre-analysis, the fidelity check for the measurement time frame being positive, the processor providing the positive result for the fidelity check upon the plurality of measured blood glucose values comprising a set of measured blood glucose values being representative for the measurement time frame such that the statistical blood glucose level information, represented by the analysis data and provided by the processor on the display as the output analysis data, is only based on the measured blood glucose values which have a positive fidelity check, and wherein upon the pre-analysis providing that the plurality of measured blood glucose values is only representative for a time period shorter than the measurement time frame, an adjusted time frame which corresponds to the shorter time period identified by the processor is then used by the processor as the measurement time frame for the fidelity check such that the statistical blood glucose level information based on the whole set of the measured blood glucose values and displayed on the display by the processor as the output analysis data is representative only for the time period shorter than the measurement time frame.

20. The method of claim 19, wherein the step of performing an analysis of the plurality of measured blood glucose values and/or the step of providing output analysis data are performed by the processor upon additionally, in the step of performing the pre-analysis an adherence check being positive, the processor providing a positive result for the adherence check upon the plurality of measured blood glucose values being collected in accordance with a testing scheme, and wherein at least part of the adherence check and the fidelity check are simultaneously run.

* * * * *